United States Patent
Moubayed et al.

(10) Patent No.: US 7,565,301 B2
(45) Date of Patent: Jul. 21, 2009

(54) SYSTEM AND METHOD FOR REMOTELY OPERATING A PERISTALTIC PUMP

(75) Inventors: Ahmad-Maher Moubayed, Mission Viejo, CA (US); David White, San Juan Capistrano, CA (US); Linda Thomas, Laguna Niguel, CA (US); Chuck Grey, Irvine, CA (US); Mehryar Michael Parsee, Los Angeles, CA (US)

(73) Assignee: Curlin Medical Inc., East Aurora, NY (US)

( * ) Notice: Subject to any disclaimer, the term of this patent is extended or adjusted under 35 U.S.C. 154(b) by 1120 days.

(21) Appl. No.: 10/205,965

(22) Filed: Jul. 26, 2002

(65) Prior Publication Data

US 2004/0019607 A1      Jan. 29, 2004

(51) Int. Cl.
*A61B 5/00* (2006.01)
*G06F 19/00* (2006.01)
(52) U.S. Cl. .................. 705/3; 705/2; 367/76; 604/65; 604/151; 604/900
(58) Field of Classification Search ...................... 705/2, 705/3; 604/131, 151 T, 900, 65, 151; 367/76
See application file for complete search history.

(56) References Cited

U.S. PATENT DOCUMENTS

| | | | |
|---|---|---|---|
| 2,877,714 A | 3/1959 | Sorg et al. | |
| 3,172,367 A | 3/1965 | Kling | |
| 4,671,792 A | 6/1987 | Borsanyi | |
| 4,756,706 A * | 7/1988 | Kerns et al. | 604/66 |
| 4,886,431 A | 12/1989 | Soderquist et al. | |
| 4,893,991 A | 1/1990 | Heminway et al. | |
| 5,681,285 A * | 10/1997 | Ford et al. | 604/151 |
| 5,814,015 A | 9/1998 | Gargano et al. | |
| 6,164,921 A | 12/2000 | Moubayed et al. | |
| 6,269,340 B1 * | 7/2001 | Ford et al. | 705/3 |
| 6,371,732 B1 | 4/2002 | Moubayed et al. | |
| 6,799,149 B2 | 9/2004 | Hartlaub | |
| 2001/0031944 A1 | 10/2001 | Peterson et al. | |
| 2002/0049684 A1 | 4/2002 | Nagamoto et al. | |
| 2004/0176984 A1 * | 9/2004 | White et al. | 705/2 |

FOREIGN PATENT DOCUMENTS

WO     WO 00/18449     4/2000

* cited by examiner

*Primary Examiner*—Gerald J. O'Connor
*Assistant Examiner*—Michelle Le
(74) *Attorney, Agent, or Firm*—Hodgson Russ LLP (57) ABSTRACT

A method of storing on a remote storage device protocol information for a drug for administration via a peristaltic pump is disclosed. A communications path between the peristaltic pump and the remote storage device is provided. The protocol information for the drug is entered into the peristaltic pump. The protocol information is transferred from the peristaltic pump to the remote storage device. The protocol information for the drug is stored on the remote storage device. History information may be retrieved from the peristaltic pump. A user request is received requesting retrieval of history information from the peristaltic pump. A pump request is formatted to retrieve history information. The pump request to receive history information is transmitted to the peristaltic pump. The history information is received from the peristaltic pump. The history information is displayed and stored.

12 Claims, 9 Drawing Sheets

SYSTEM AND METHOD FOR REMOTELY OPERATING A PERISTALTIC PUMP

CROSS-REFERENCE TO RELATED APPLICATIONS (Not Applicable)

STATEMENT RE: FEDERALLY SPONSORED RESEARCH/DEVELOPMENT (Not Applicable)

Compact Disc Appendix

The specification of the present application includes a compact disc appendix which is submitted herewith and incorporated by reference herein. The compact disc appendix includes a total of two (2) files, the first file is titled "350-9008B CMS User Manual", created on Friday, Jun. 21, 2002, with a size of 891,000 bytes and the second file is titled "Curlin Medical 4000 Peristaltic Pump", created on Monday Apr. 29, 2002, with a size of 2,243,000 bytes. The file titled Curlin 4000 Manual R5-E is a User's Manual for the Curlin Medical 4000 Peristaltic Pump and the file titled 350-9008B CMS User Manual is a User's Manual for the Curlin Medical Clinical Management System which can be used with the Curlin Medical 4000 Peristaltic Pump.

BACKGROUND OF THE INVENTION

The present invention relates generally to medical infusion pumps and more particularly to a system and method for remotely controlling a peristaltic pump.

Traditionally infusion pumps have been used to deliver medications and fluids to patients, intravenously subcutaneously or Epidural, according to a controlled rate and dose schedule. Such infusion or peristaltic pumps are known in the art. Peristaltic pumps may be linear, such as those described in U.S. Pat. No. 2,877,714 (Sorg, et. al), U.S. Pat. No. 4,671,792 (Borsannyi), U.S. Pat. No. 4,893,991 (Canon), rotary, such as those described in U.S. Pat. No. 4,886,431 (Soderquist et al.) and U.S. Pat. No. 3,172,367 (Kling) or curvilinear, such as is described in U.S. Pat. No. 6,164,921 (Moubayed et al.).

The pump is normally programmed by a clinician based on a specific patient prescription. The pump is traditionally programmed through a user interface keypad on the pump.

There have been some efforts in the past to establish capabilities of remotely programming the pump through a modem and transferring data through telephone lines. For example, Mediview, which is currently owned by Baxter, provides remote programming capabilities of the Homerun 6060 pump through a modem and telephone line, It allows the clinician to view, at a remote location, the 6060 pump simulated on a computer monitor with its display and keypad. The clinician can view the display of the remote pump on a computer monitor and can interact with the pump using a mouse and keyboard. Remote programming systems, such as those described above may be difficult to program and do not reduce infusion errors.

Thus, there is a need for a system and method for programming a peristaltic pump which reduces infusion errors. The system should also be easy to program, i.e., should not require significant training by the clinician.

BRIEF SUMMARY OF THE INVENTION

An aspect of the present invention may be regarded as a method of storing on a remote storage device protocol information for a drug for administration via a peristaltic pump. The method provides a communications path between the peristaltic pump and the remote storage device. The protocol information for the drug is entered into the peristaltic pump. The protocol information is transferred from the peristaltic pump to the remote storage device. The protocol information for the drug is stored on the remote storage device.

The protocol information may be stored in a drug library on the remote storage device. The protocol information may be selected from the drug library and sent to the peristaltic pump for administration to a patient. The protocol information may be copied from the drug library to a patient library. The protocol information may be exported from the drug library. The exported protocol information may be sent to another user, for example, via e-mail. The protocol information in the drug library may be edited.

The protocol information may be stored in a patient library on the remote storage device. The protocol information may be selected from the patient library and sent to the peristaltic pump for administration to a patient. The protocol information may be exported from the patient library. The protocol information in the patient library may be edited.

The protocol information for the drug may include associated warnings and precautions.

The remote storage device is a personal computer, such as a laptop computer. The remote storage device may be a hand-held storage device, such as a Personal Digital Assistant (PDA).

A current date/time and/or maintenance date may be entered.

Calibration functions may be invoked.

Another aspect of the present invention may be regarded as a method for receiving history information from a peristaltic pump. A user request is received requesting retrieval of history information from the peristaltic pump. A pump request is formatted to retrieve history information. The pump request to receive history information is transmitted to the peristaltic pump. The history information is received from the peristaltic pump. The history information is displayed.

The history information may be all of the history information stored in the peristaltic pump. The history information may be the latest prescription. The history information may be a predefined amount of history information, e.g., four kilobytes. The history information may be printed or exported for e-mail to others.

BRIEF DESCRIPTION OF THE DRAWINGS

These as well as other features of the present invention will become more apparent upon reference to the drawings wherein.

DETAILED DESCRIPTION OF THE INVENTION

Figure 1A:
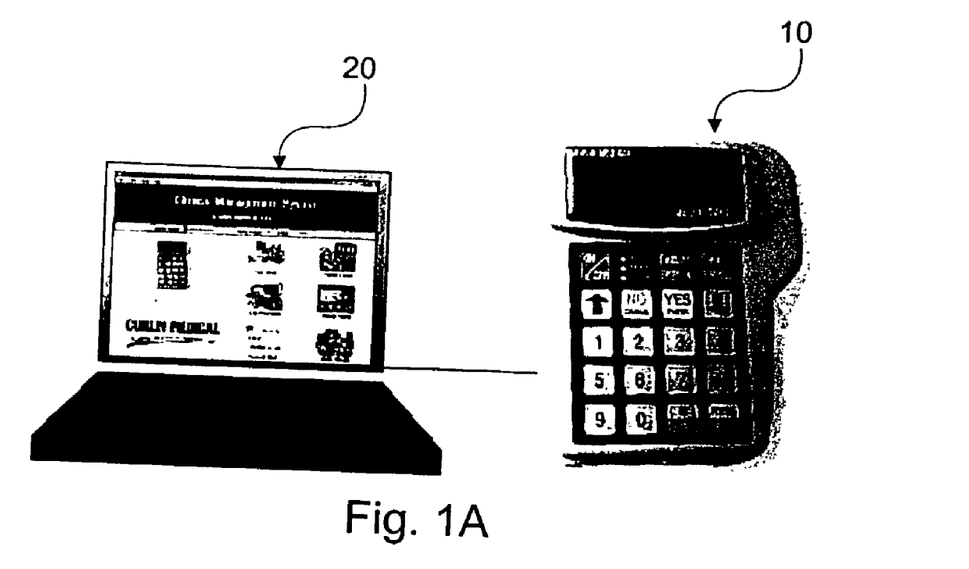
FIG. 1A illustrates a first embodiment of the present invention wherein a peristaltic pump is in communication with a laptop computer.
Figure 1B:
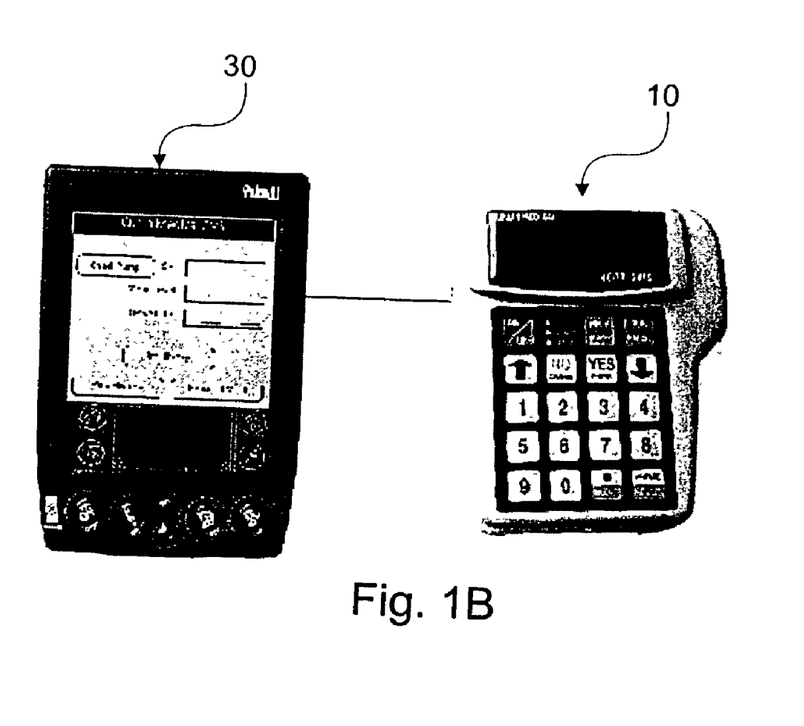
FIG. 1B illustrates a second embodiment of the present invention wherein the peristaltic pump of FIG. 1A is in communication with a handheld computing device.

Referring now to the drawings wherein the showings are for purposes of illustrating preferred embodiments of the present invention only, and not for purposes of limiting the same, FIGS. 1A and 1B illustrate a persistaltic pump in communication with a computer capable of programming the pump. The particular pump shown in the Figures is marketed by Curlin Medical of Huntington Beach, Calif. and is described in U.S. Pat. No. 6,164,921, the disclosure of which is expressly incorporated herein by reference. However, use of other ambulatory pumps is contemplated herein. Pumps, such as the one shown in FIGS. 1A and 1B are typically standalone devices used to administer medication to a patient. The pump 10 shown in FIGS. 1A and 1B can be used as a stand-alone pump. Additionally, the pump shown in FIGS. 1A and 1B can communicate with a computer, such as a laptop computer 20 (shown in FIG. 1A) or a handheld computer, such as a personal digital assistant (PDA) 30 (shown in FIG. 1B).

The present invention helps reduce the risk of medication errors, reduces staff costs by enabling point-and-click, time-efficient programming of the pump, facilitates remote monitoring of the infusion process, provides an audit trail for billing, validation and archival purposes, and easily integrates into existing systems. The data management functions allow the clinician the ability to create, select, and use protocols and prescriptions, select and transfer personalized prescriptions to a PDA/Palm™ device, provide a "Drug Precautions" page for warnings, indications and instructions, compile data for further analysis, retrieve patient-history files, and generate customized reports from a PC or Palm device.

Preferably, the computing device 20 is a personal computer (PC) with at least a 486 Intel® processor with a system speed of at least 90 MHz (megahertz). In preferred embodiments, the computing device 20 uses a Windows® operating system, such as Windows® 95, 98, ME, 2000 or NT. The computing device 20 should have at least thirty-two (32) MB (megabytes) of random access memory (RAM) and at least eight (8) MB of available storage space. The computing device 20 preferably includes a compact disc read-only memory (CD-ROM) drive. Preferably, the computing device 20 includes a graphics card that is capable of a pixel resolution of 800×600 or better (e.g., super video graphics array (SVGA) or better). In addition to a keyboard, the computing device 20 preferably includes a pointing device, such as a mouse.

The pump shown in FIGS. 1A and 1B, like prior art pumps includes logic (software) for managing the pump.

In exemplary embodiments of the present invention, the computer 20 stores a drug library and a patient library. The drug library stores protocols classified by drug name, programmer name (person who stored the protocol), and creation date. A prescription or protocol can be selected from those stored in the drug library. The prescription can then be sent to the pump attached to the computer. The protocol is then uploaded to the pump.

Figure 2:
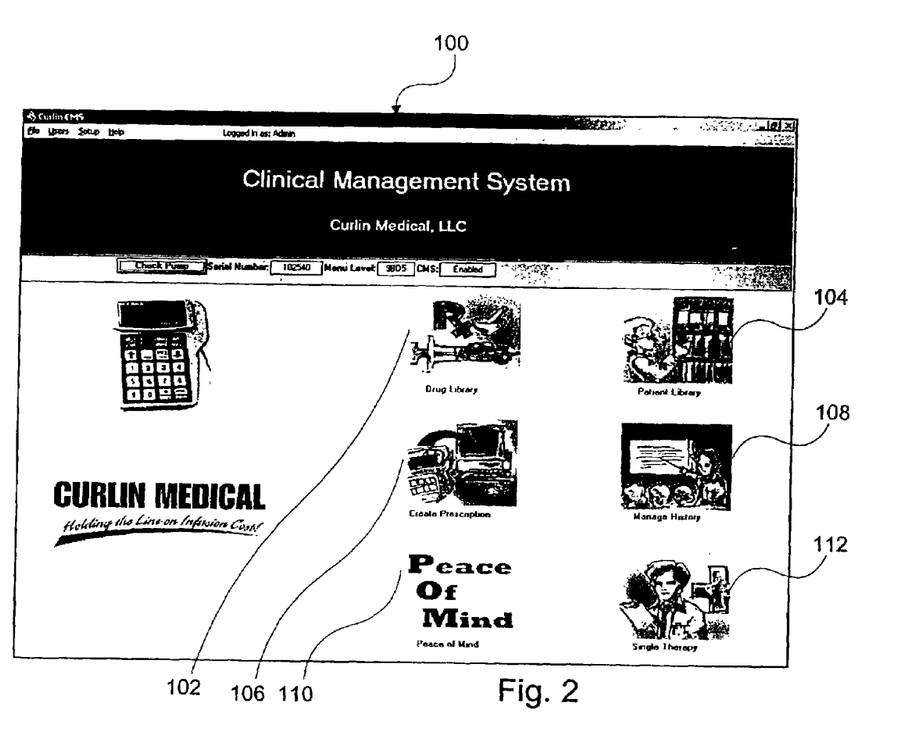
FIG. 2 illustrates an example screen display showing the major functions of one embodiment of the present invention.

FIG. 2 illustrates an example screen display showing the major functions of one embodiment of the present invention. Preferably, upon starting the program, the user is asked to enter a password. Details in setting up passwords and entering and validating password is not explained in further detail herein as techniques known in the art can be used for security aspects of the present invention including a user login function.

The exemplary screen display 100 shown in FIG. 2 includes controls to access the major functions of the present invention. In the illustrated example, graphical depictions of the function are selected to invoke the various functions. It will be appreciated that other user interface controls, such as menus, could be used to access the functions. The selections available from the main menu shown in FIG. 2 include: Drug Library 102, Patient Library 104, Create Prescription 106, Manage History 108, Peace of Mind 110 and Single Therapy 112. Each of theses functions is briefly summarized next and described in more detail later.

Pressing the Drug Library button 102 invokes the drug library function which allows the user to store and access protocols. Pressing the Patient Library button 102 invokes the patient library function which allows the user to store and access (e.g., copy and export) patient specific prescriptions. Pressing the Create Rx button 104 invokes the create prescription function which allows the user to enter and store information in the drug library or the patient library. Pressing the Manage History button 106 invokes the manage history function which allows the user to download the pump history for archiving, documentation, review or analysis. Pressing the Peace of Mind button 108 invokes the peace of mind function which downloads a recently programmed therapy for documentation, validation or verification. Pressing the Single Therapy button 110 invokes the single therapy function which converts the pump into a PCA, TPN, continuous, intermittent, or variable therapy pump for manual programming.

Figure 3:
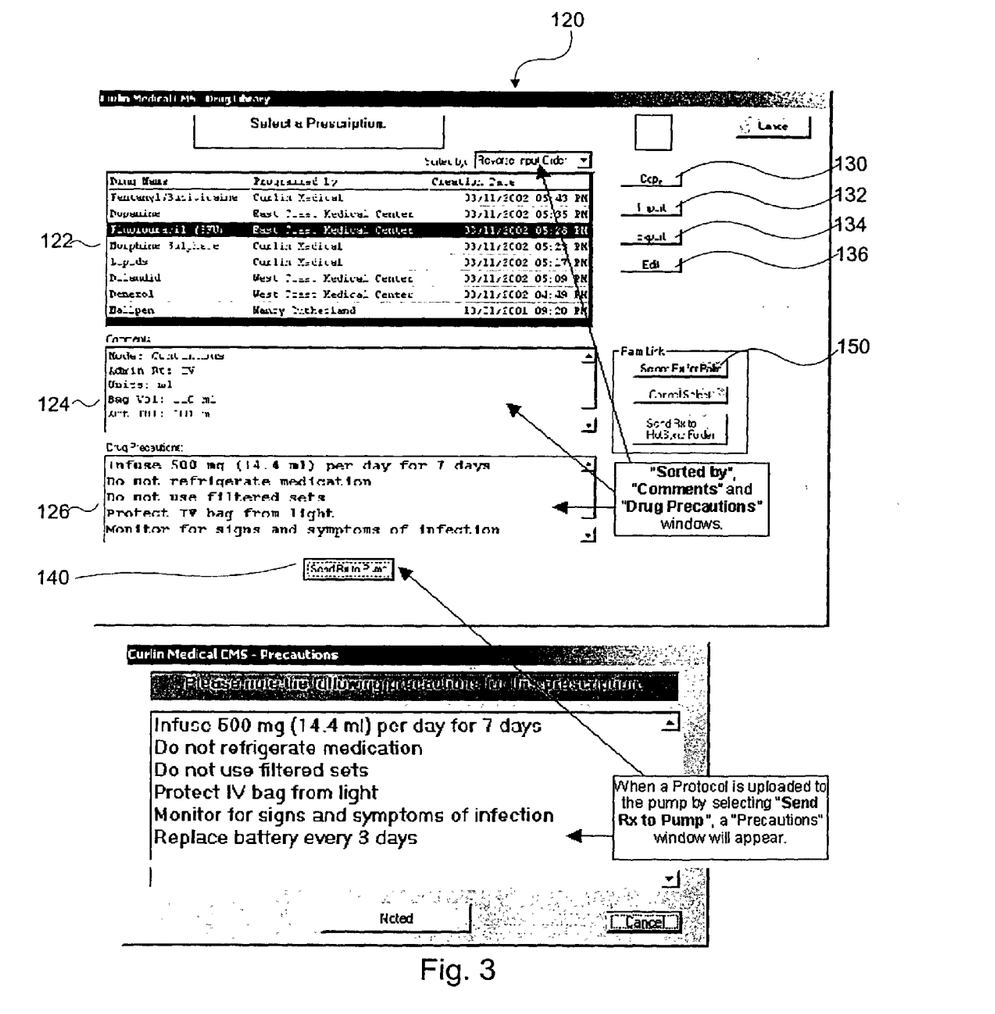
FIGS. 3-9 illustrate exemplary screen displays for performing the various functions available from the display shown in FIG. 2.

If the user presses the Drug Library button 102, an exemplary Drug Library Display 120 such as the one shown in FIG. 3 is displayed so that the user can view or edit information for the prescription that was entered during create Rx. In the example shown, there is a list of stored protocols 122 which are identified by a drug name, programmer and creation date. One of the stored protocols can be selected. Detailed information is then shown for the selected protocol. The detailed information includes comments 124 and drug precautions 126. The display includes controls, such as buttons, that allow the user to manipulate the data in the drug library.

In the exemplary embodiment, the user can press a Copy button 130 which allows the user to copy a protocol from the drug library to the patient library. When the copy button 130 is pressed, a window is displayed prompting for a patient's name. Entry and acceptance of a valid patient name causes the selected protocol to be copied to the patient library and stored under the entered patient's name.

Pressing an Import button 132 allows the user to import a protocol. This allows the user to store appropriately formatted files into the drug library. The files may be sent by another user.

Pressing an Export button 134 allows the user to export a selected protocol. The user can export the protocol to another user. In exemplary embodiments, the protocol is exported by sending it to the desired user via e-mail.

Pressing an Edit button 136 allows the user to edit an existing protocol. In exemplary embodiments, selection of the edit function causes two additional controls, e.g., buttons, to be displayed, namely, Delete and Save. The user can then edit the comments and/or precautions fields and save them by pressing the save button, if desired. In exemplary embodiments, the drug name, programmed by and creation date fields cannot be edited. The user may delete a protocol, if desired, by pressing the Delete button.

The user may also send the prescription to the pump by pressing a Send Rx to Pump button 140. Sending a prescription to the pump programs the pump with the prescription. Pressing the Send Rx to Pump button 140 causes the precaution window to display the precaution information for the protocol. The administrator of the prescription must review the precautions and indicate that the precautions have been reviewed by pressing the "Noted" button.

The user can also opt to Send a Prescription to the Palm™ by pressing the Select Rx for Palm button 150. In exemplary embodiments, selection of this function saves selected protocols into a directory for transfer to a Palm™ device. A cable is connected from the computer to the Palm™ device. In exemplary embodiments, the user selects the prescription to be sent to a HotSync folder. The files in the HotSync folder can then be selected for transfer to the Palm™ device. In exemplary embodiments, all of the protocols being transferred to the Palm™ device are stored in one file, for example, a file named Patient.pdb. This file is then transferred to the Palm™ device. In exemplary embodiments, if there is an existing Patient.pdb file, it will be written over by the new file. Thus, the user must transfer all of desired protocols to the Palm™ device as the current ones will be overwritten.

Figure 4:
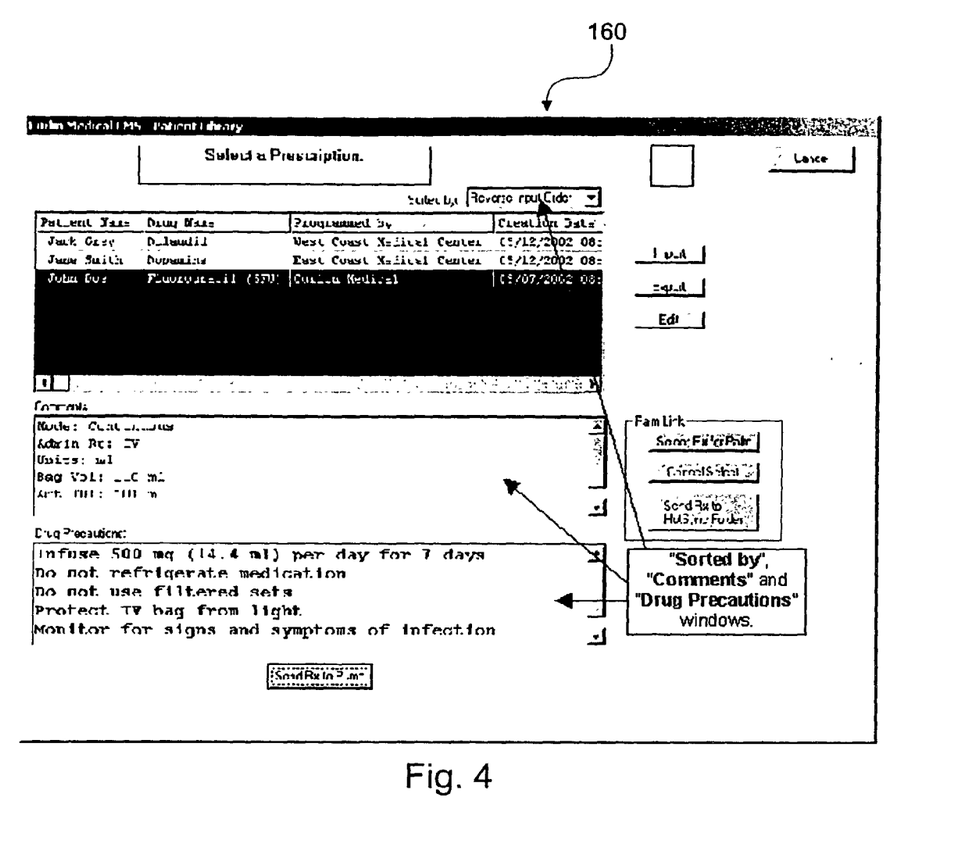

If the user presses the Patient Library button 104, a patient library display 160 is displayed. In exemplary embodiments, such as the one shown in FIG. 4, the patient library display 160 and functions (invoked by controls, such as buttons) are similar to those for the drug library. As with the drug library, the user can import, export or edit entries in the patient library. The user can send a prescription to the pump or transfer prescriptions to the Palm™ device.

Figure 5:
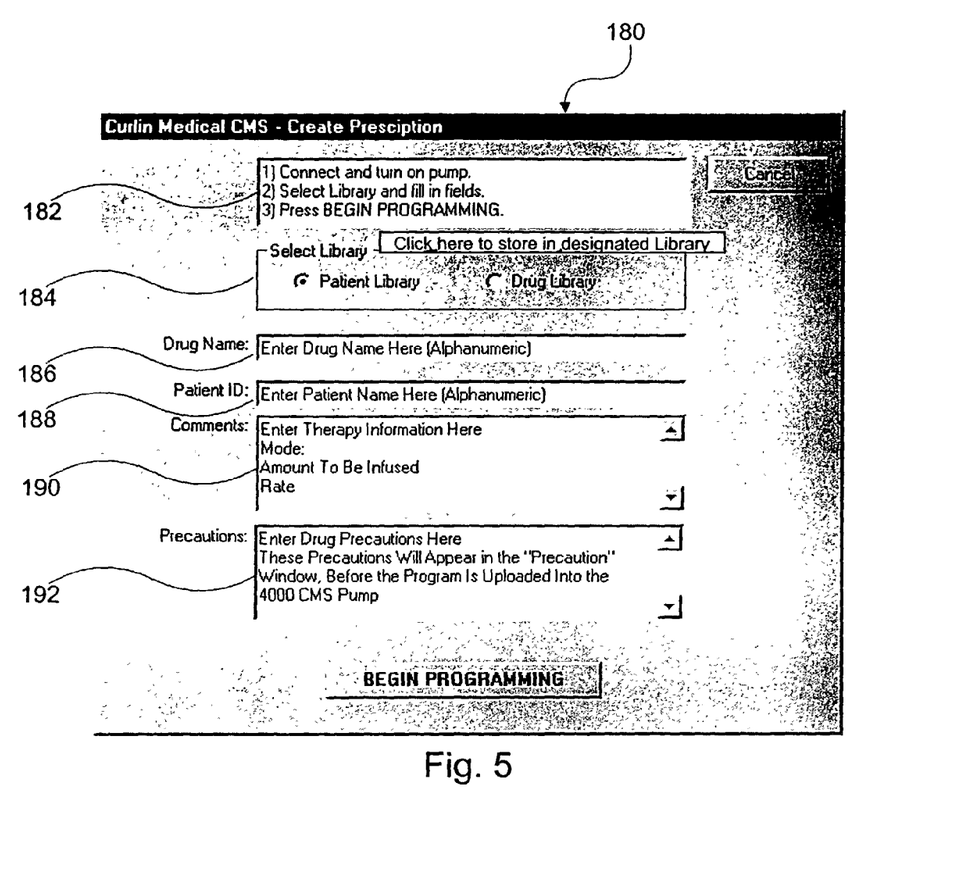

Creating a prescription allows the user to store prescription information in the drug library or the patient library. This information is uploaded from the pump. The user presses the Create Prescription button 106 from the main display window 100. A create prescription window 180 such as the one shown in FIG. 5 is displayed. The exemplary screen display shown in FIG. 5 provides the user with an instruction window 182 which tells the user to: (1) connect and turn on the pump; (2) select library and fill in fields; and (3) program the pump.

A cable is used to connect the pump, for example, Curlin Medical 4000 CMS pump 10 is connected to the PC 20, by inserting the cable in the serial port of the PC. The user selects the desired library 184, i.e., the drug library or the patient library, for storing the protocol to be uploaded from the pump. The user also enters a drug name 186, a patient ID 188, comments 190 and precautions 192.

The user then presses a Begin Programming button 194 to begin programming the pump. The pump is programmed the same as during stand-alone operation of the pump. For example, if the pump is a Curlin Medical 4000 Plus pump, the pump is programmed according to the directions for that particular pump. The user's manual for the Curlin Medical 4000 Plus pump is included as a compact disc appendix and is incorporated herein by reference.

Figure 6:
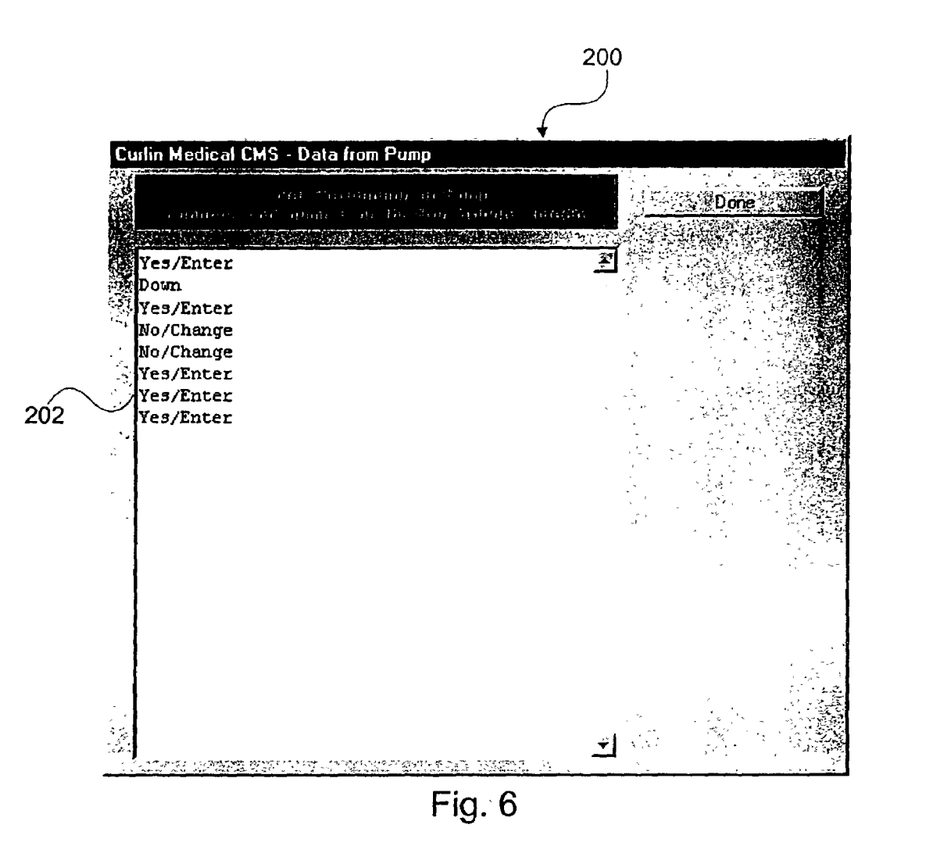

In exemplary embodiments, such as the one shown in FIG. 6, protocol information, including keystrokes that are used when programming the pump, is stored. For example, when a menu is displayed and the user scrolls down, "DOWN" is stored in the protocol file. Thus, when the information is uploaded to the pump, it is as if a user were using the keypad to enter the information directly into the pump except that the information is actually transmitted from the computer via the cable that connects the pump to the computer.

By way of example, the aforementioned User's Manual for the Curlin Medical Clinical Management System provides instructions for creating a Prescription as follows:

"Create Prescription is used to generate protocols/prescription for the Drug or Patient Library.

Note To ensure successful upload of protocol/prescription, create protocols and prescriptions that are ALERT free.

To create a protocol/prescription, perform the following steps:

1 Connect a 4000 CMS pump to the Serial port on the PC, using a Curlin Medical 'Data Interface cable for PC' (catalog number 340-2018);

2 Turn the pump on;

3 Launch the CMS program;

4 Make sure that there is connection (see Checking the Connection)

5 Press the Create Prescription button;

6 Select the appropriate library for storing the program.

Depending upon the selection, the following information is required:

a) A patient name if the Patient Library is selected (limit 50 characters);

b) A drug name if the Drug Library is selected (limit 50 characters).

You may start by describing the prescription and drug precautions (maximum of 32,000 characters each) in the appropriate sections at this time or edit them subsequently in the appropriate Library. However, the patient and drug name, once saved, cannot be changed but the protocol/prescription may be deleted.

It is helpful to think ahead about the protocol/prescription that you intend to create, and have all the relevant information on hand. When ready, press the 'BEGIN PROGRAMMING' button, then enter the program on the Curlin Medical 4000 CMS pump. A 'Data from Pump' window will appear, displaying the key strokes used to program the prescription.

The CMS protocol/prescription is created manually, on the Curlin Medical 4000 CMS pump, and continued until the 'Run Option' screen is reached.

When finished programming, click on the 'Done' button on the 'Data from Pump' computer window. At this point the program will provide a warning asking you to verify that the pump is on the 'Run Options' screen; and the option to press 'Done' or to 'Continue Programming'.

Check to make sure that the pump is indeed on the 'Run Option Screen'. A sample of the 'Run Options Screen' on the Curlin Medical 4000 CMS pump is provided below.

If so, press 'Done' to save the prescription; otherwise press 'Continue Programming' and finish the prescription.

For additional safety, run the program that you have created to ensure that it complies with your protocol/prescription.

Note For programming help, or how to use the Curlin Medical 4000 CMS Pump, please refer to your User's Manual for use with the 4000 Plus™ and 4000 CMS™ Ambulatory Infusion Pumps."

The computer stores history files. Peace of mind files include the latest programmed prescription.

Figure 7:
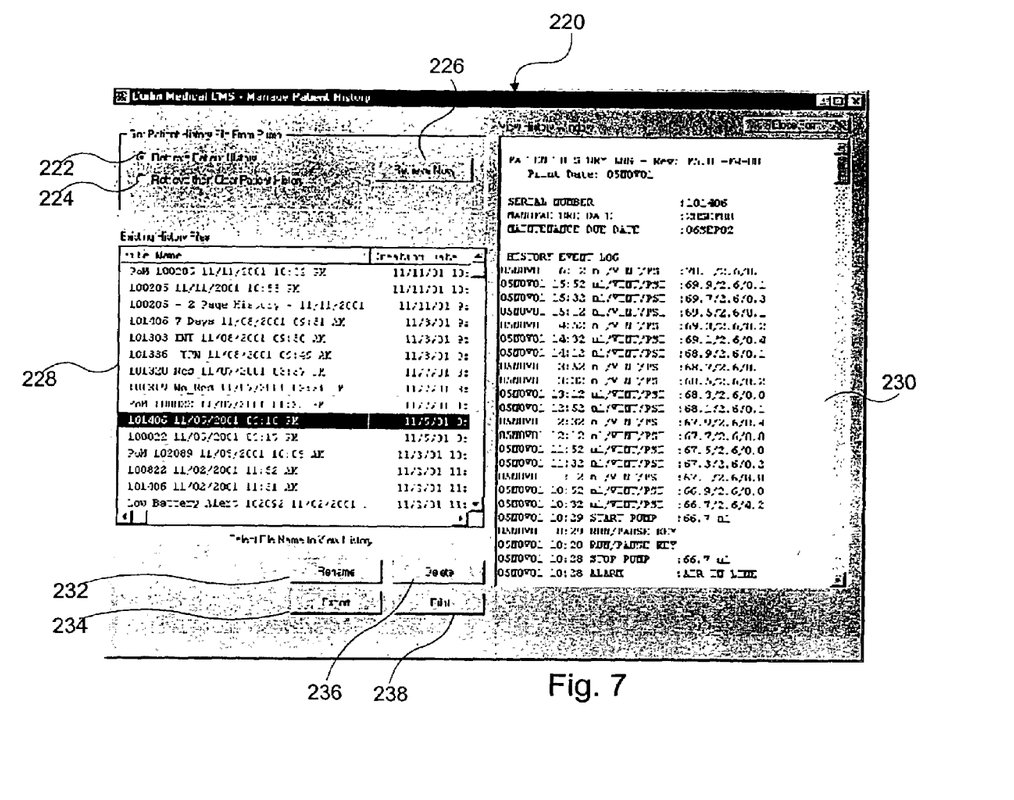

If the user presses the Manage History button 108, the manage history function is invoked and all of the information stored in the pump 10 is downloaded to the computer 20. A manage patient history display 220 such as the one shown in FIG. 7 is displayed. The user can either choose to retrieve the patient history 222 or to retrieve and then clear the patient history 224. If clear the patient history is selected, the history file will be deleted from the pump 10 after it is downloaded to the computer 20. After selecting one of these options, the user presses a Retrieve Now button 226 to retrieve the data from the pump. The names and creation dates of the downloaded history files are displayed in an existing history files window 228. The user can select a history file from the existing history file window 228. The data in the selected file is then displayed in a view history window 230. There are also controls (e.g., buttons) that allow the user to rename 232, export 234, delete 236 or print 238 a selected history file.

Figure 8:
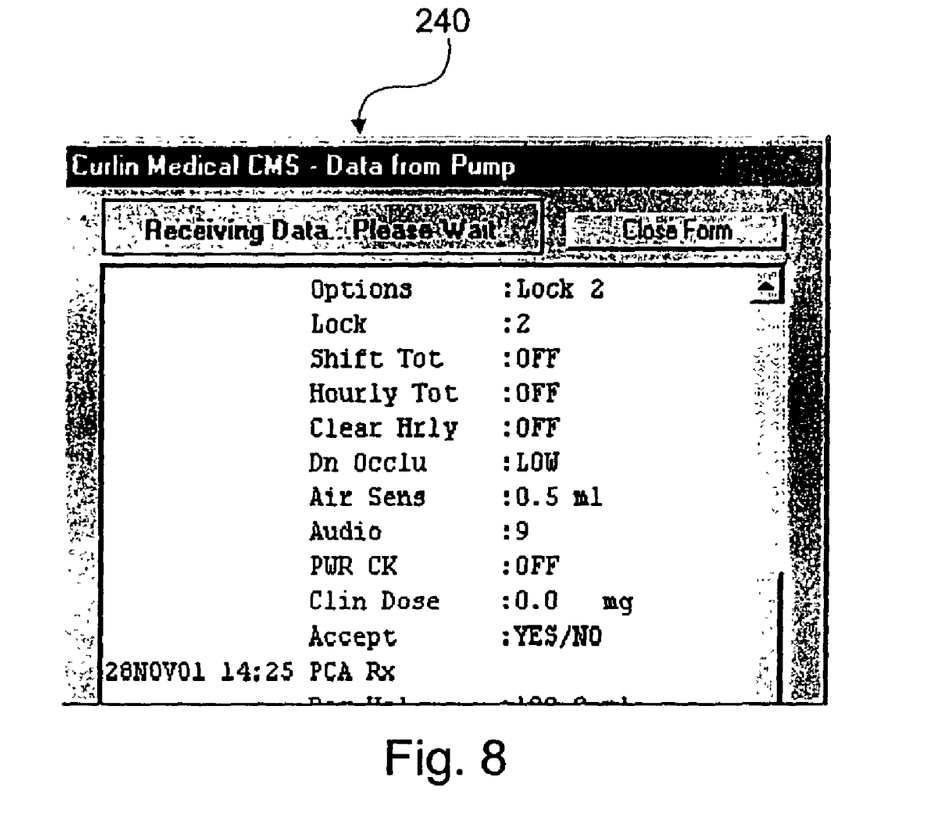
Figure 9:
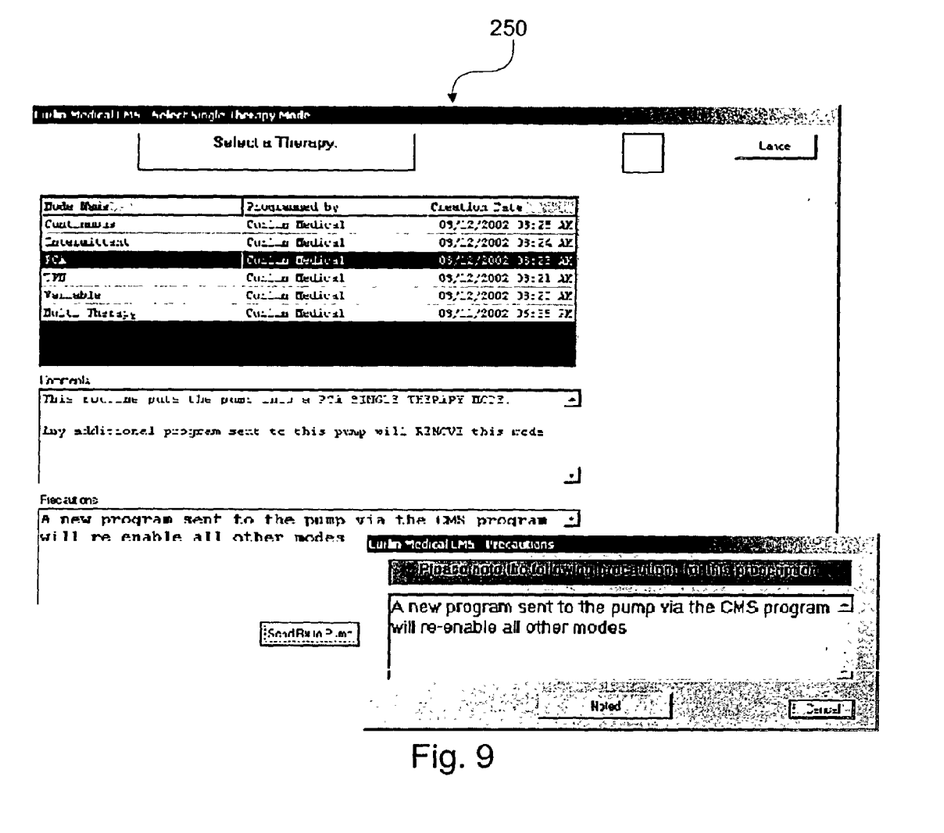

If the user presses the Peace of Mind button 112, a peace of mind function is invoked. The peace of mind function downloads and displays the most recently programmed therapy. This provides the clinician with proof (or peace of mind) that the therapy was uploaded into the pump. In exemplary embodiments, this features downloads the most recent four (4) kilobytes of data from the pump. An exemplary screen display 240 showing peace of mind data is shown in FIG. 8.

The present invention also allows the pump to be utilized as a single therapy device. When the user presses the Single Therapy button 112, all but one therapeutic mode on the pump are disabled. For example, some hospitals only need a single mode, such as PCA. This feature can be used when the pump is being manually programmed. In exemplary embodiments, the user can select any available therapeutic mode as the single mode therapy, for example, Continuous, Intermittent, Multi Therapy, PCA, TPN, or Variable. The pump can be removed from single therapy mode manually or by selecting multi therapy.

Various maintenance activities may be performed on the pump using the present invention. For example, a current date/time may be entered and/or a maintenance date may be entered. The present invention may also be used to invoke calibration functions on the pump.

In exemplary embodiments, a palm computing device 30 may be used to perform a subset of the operations that can be performed by larger computing devices, such as a laptop computer 20. The Palm system can be used to program a pump 10 or to retrieve information from the pump. Protocols or prescriptions can be transferred to the PDA 30 from the PC 20 for bedside pump programming. Infusion information gathered by the pump 10 can be downloaded for later analysis.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method of creating a patient prescription program or a drug protocol program for controlling a peristaltic pump, the method comprising the steps of:
    receiving a selection of a patient library or a drug library inputted to the computer system by a user;
    verifying that a peristaltic pump is in communication with a computer system remote from the pump;
    receiving program information inputted to the computer system by a user, the program information including a patient name or a drug name, comment information, and precaution information;
    receiving a begin command inputted to the computer system by a user, the begin command indicating that the computer system is ready to receive keystroke data from the pump;
    receiving at the computer system keystroke data from the pump as the pump is programmed by a user operating keys on the pump;
    displaying each individual keystroke datum in a user-readable format on the computer system as the keystroke datum is received at the computer system;
    storing the program information and the keystroke data on the computer system in association with one another as a patient prescription program in the patient library or a drug protocol program in the drug library which may be recalled later to remotely control the peristaltic pump; and
    providing a directory on the computer system of the patient library or the drug library whereby the user may select a stored program, and the associated comment information and precaution information of the selected program, but not the keystroke data of the selected program, are displayed for user editing.

2. The method according to claim 1, further comprising the step of receiving a done command inputted to the computer system by a user prior to the step of storing the program information and the keystroke data.

3. The method of claim 2, further comprising the steps of:
    prompting a user, in response to the done command, to confirm that a predetermined screen is displayed on the pump; and
    receiving a confirmation command inputted to the computer system by a user to indicate that the predetermined screen is displayed on the pump.

4. The method according to claim 1, wherein the stored patient prescription program or drug protocol program is used to remotely control a peristaltic pump by performing the steps of:
    displaying on a computer system remote from the pump a directory representing contents of a program library;
    receiving a program selection command inputted to the computer system by a user, the program selection command indicating a chosen patient prescription program or drug protocol program from the program library; and
    uploading the chosen program from the computer system to the pump, the chosen program including keystroke data originating from and corresponding to sequential operation of keys on the pump, wherein the pump is remotely programmed the same as the pump would be programmed for stand-alone operation.

5. The method according to claim 4, further comprising the step of verifying that the pump is in a mode other than an infusing mode prior to uploading the chosen program.

6. The method according to claim 4, wherein the chosen program includes comment information, and the method further comprises the step of displaying the comment information on the computer system.

7. The method according to claim 4, wherein the chosen program includes precaution information, and the method further comprises the step of displaying the precaution information on the computer system.

8. The method according to claim 7, further comprising the step of receiving a precautions noted command inputted to the computer system by a user in response to the displayed precaution information.

9. The method according to claim 4, further comprising the steps of:
    prompting a user to review the uploaded chosen program on the pump; and
    receiving a confirmation command inputted to the computer system by a user to acknowledge that the chosen program should be reviewed on the pump.

10. The method according to claim 4, wherein the computer system includes a personal computer.

11. The method according to claim 10, wherein the computer system further includes a handheld computer communicating with the personal computer.

12. The method according to claim 11, wherein the directory is displayed on the handheld computer and the program selection command is inputted to the handheld computer.

* * * * *